United States Patent
Giralt et al.

(10) Patent No.: US 12,307,791 B2
(45) Date of Patent: May 20, 2025

(54) METHOD FOR DETERMINING A DROWSINESS LEVEL OF A MOTOR VEHICLE DRIVER

(71) Applicants: Continental Automotive France, Toulouse (FR); Continental Automotive GmbH, Hannover (DE)

(72) Inventors: Alain Giralt, Toulouse (FR); Martin Petrov, Toulouse (FR)

(73) Assignees: Continental Automotive France, Toulouse (FR); Continental Automotive GmbH, Hannover (DE)

( * ) Notice: Subject to any disclaimer, the term of this patent is extended or adjusted under 35 U.S.C. 154(b) by 425 days.

(21) Appl. No.: 17/296,783

(22) PCT Filed: Dec. 13, 2019

(86) PCT No.: PCT/EP2019/085147
§ 371 (c)(1),
(2) Date: May 25, 2021

(87) PCT Pub. No.: WO2020/120760
PCT Pub. Date: Jun. 18, 2020

(65) Prior Publication Data
US 2022/0027646 A1 Jan. 27, 2022

(30) Foreign Application Priority Data

Dec. 13, 2018 (FR) .................................. 1872824

(51) Int. Cl.
*G06V 20/59* (2022.01)
*B60W 40/08* (2012.01)
(Continued)

(52) U.S. Cl.
CPC .......... *G06V 20/597* (2022.01); *B60W 40/08* (2013.01); *G06F 18/214* (2023.01); *G08B 21/06* (2013.01);
(Continued)

(58) Field of Classification Search
CPC .... G06V 20/597; B60W 40/08; B60W 50/14; B60W 60/0059; B60W 2040/0827;
(Continued)

(56) References Cited

U.S. PATENT DOCUMENTS 5,813,993 A 9/1998 Kaplan et al.
9,483,739 B2 * 11/2016 Haws ...................... G06F 17/18
(Continued)

FOREIGN PATENT DOCUMENTS

| CN | 101030316 A | 9/2007 |
|---|---|---|
| CN | 103042922 A | 4/2013 |

(Continued)

OTHER PUBLICATIONS

D'Orazio T., et al., "A visual approach for driver inattention detection," Apr. 17, 2007, vol. 40(8), pp. 2341-2355, XP022031756, Pattern Recognition, Elsevier, GB. (Year: 2007).*
(Continued)

*Primary Examiner* — Nancy Bitar
*Assistant Examiner* — Dustin Bilodeau
(74) *Attorney, Agent, or Firm* — Buchanan Ingersoll & Rooney PC

(57) ABSTRACT

A method for determining a level of drowsiness of a driver of a motor vehicle on the basis of a predetermined image analysis algorithm, the vehicle including a camera and a computer, the computer implementing the predetermined algorithm on the basis of a set comprising at least one parameter relating to the attitude of the driver, the method,
(Continued)

implemented by the computer, including a phase of learning and a phase of monitoring the state of the driver.

18 Claims, 2 Drawing Sheets

(51) Int. Cl.
*B60W 50/14* (2020.01)
*B60W 60/00* (2020.01)
*G06F 18/214* (2023.01)
*G08B 21/06* (2006.01)

(52) U.S. Cl.
CPC ..... *B60W 2040/0827* (2013.01); *B60W 50/14* (2013.01); *B60W 60/0051* (2020.02); *B60W 60/0059* (2020.02); *B60W 2420/403* (2013.01); *B60W 2540/221* (2020.02); *B60W 2540/223* (2020.02); *B60W 2540/229* (2020.02)

(58) Field of Classification Search
CPC ....... B60W 2420/42; B60W 2540/221; B60W 2540/223; B60W 2540/229; G06F 18/214; G08B 21/06; A61B 5/1128; A61B 5/18; A61B 5/4809; A61B 5/6893
See application file for complete search history.

(56) References Cited

U.S. PATENT DOCUMENTS

| | | |
|---|---|---|
| 2003/0169907 A1 | 9/2003 | Edwards et al. |
| 2013/0093888 A1 | 4/2013 | Kim |
| 2019/0102638 A1* | 4/2019 | Nanu ................... G06V 20/597 |
| 2020/0290628 A1 | 9/2020 | Pinoteau |

FOREIGN PATENT DOCUMENTS

| | | |
|---|---|---|
| FR | 3048542 A1 | 9/2017 |
| WO | 2018118958 A1 | 6/2018 |

OTHER PUBLICATIONS

D'Orazio. T., et al., "A visual approach for driver inattention detection," Apr. 17, 2007, vol. 40(8), pp. 2341-2355, XP022031756, Pattern Recognition, Elsevier, GB.
International Search Report and Written Opinion for International Application No. PCT/EP2019/085147, mailed Mar. 11, 2020, with partial English translation, 12 pages.
International Search Report and Written Opinion for International Application No. PCT/EP2019/085147, mailed Mar. 11, 2020, 17 pages (French).
Office Action (Notification under Article 94(3) EPC) issued Nov. 23, 2023, by the European Patent Office in corresponding European Patent Application No. 19 829 064.5-1205 and an English machine translation of the Office. Action. (16 pages).

* cited by examiner

METHOD FOR DETERMINING A DROWSINESS LEVEL OF A MOTOR VEHICLE DRIVER

CROSS REFERENCE TO RELATED APPLICATIONS

This application is the U.S. National Phase Application of PCT International Application No. PCT/EP2019/085147, filed Dec. 13, 2019, which claims priority to French Patent Application No. 1872824, filed Dec. 13, 2018, the contents of such applications being incorporated by reference herein.

FIELD OF THE INVENTION

The invention relates to the field of assistance in the, and relates more particularly to a device and a method for driving of a motor vehicle, whether manually driven or self-driving monitoring a vehicle driver in order in particular to trigger a warning or activate an automatic driving mode in the event of drowsiness or distraction.

BACKGROUND OF THE INVENTION

Nowadays, it is known practice to equip certain motor vehicles with a monitoring device that allows the driver to be alerted if they appear distracted or if they are sinking into a state of drowsiness. This type of monitoring device comprises a camera and a computer, which processes the images generated by the camera and warns the driver in the event of drowsiness or distraction. The computer analyzes, for example, the movement of the driver's eyes, head or upper body, their facial expressions, the orientation of their head or a combination of some or all of these parameters.

In one known solution, the computer analyzes these parameters for a given duration. For example, when the computer analyzes the driver's eyes, it may in particular determine the blink frequency of the eyelids, the blink amplitude of the eyelid, the blink duration of the eyelids, etc. It then compares these values with a threshold or a range of predetermined values characterizing an alert state in order to deduce therefrom whether the driver is alert, distracted or drowsy and to warn them if necessary. For example, if the blink duration of the eyelids is shorter than 350 ms, the computer deduces therefrom that the driver is alert but if the blink duration of the eyelids is longer than 350 ms, the computer deduces therefrom that the state of drowsiness of the driver is increasing.

In the existing solutions, the thresholds or ranges of values characterizing an alert state are predetermined in the factory and stored in a memory region of the computer for use by all drivers.

However, it is apparent that there is variation between the reactions and attitudes of each driver, especially with regard to drowsiness. Specifically, for example, eyelid blink frequency, amplitude and duration may differ significantly from one driver to another.

Consequently, the device may trigger warnings, which presents an appreciable drawback, or conversely not trigger a warning even though the driver is in a distracted or drowsy state, which then presents a major drawback.

Therefore, there is a need for a solution that makes it possible to overcome these drawbacks at least in part.

SUMMARY OF THE INVENTION

An aspect of the present invention aims to provide a simple, reliable and effective solution for detecting a level of drowsiness of a vehicle driver.

To that end, a first aspect of the invention is a method for determining a level of drowsiness of a driver of a vehicle, in particular a motor vehicle, on the basis of a predetermined image analysis algorithm, said vehicle comprising a camera and a computer, said computer implementing said predetermined algorithm on the basis of a set comprising at least one parameter relating to the attitude of the driver, the method, implemented by the computer, comprising:

a learning phase performed for a predetermined period, preferably after each starting of the engine/motor of the vehicle, comprising the steps of:
  the camera generating a sequence of consecutive images (for example 10, 15, 20, 25, 30, 45, 60 . . . up to 200 images per second) of the driver,
  determining at least one characteristic point, preferably a plurality of characteristic points (for example, the corner of the eyes, the position of the pupil, etc.), of the images of the sequence of images generated,
  running the predetermined algorithm on the at least one characteristic point of the images of the sequence of images generated in a plurality of implementations performed in parallel by the computer in order to perform a plurality of diagnostics, each implementation using a different set of predetermined parameters and/or of predetermined ranges of values of parameters, so as to determine a plurality of values for each parameter of said set,
  determining a different degree of relevance for each algorithm executed, the degrees of relevance being different from one another, the highest degree of relevance being assigned to the set of predetermined parameters and/or of predetermined ranges of values of parameters that is used for which the determined values of the parameters vary the least, in order to identify the reactions and attitude of the driver in question, in particular with regard to drowsiness and fatigue, once the learning phase has ended, a phase of monitoring the state of the driver, comprising the steps of:
  the camera generating a sequence of images of the driver,
  running the predetermined algorithm on said sequence of images generated in at least one implementation performed by the computer on the basis of at least the set of parameters and/or of values of parameters having the highest degree of relevance, so as to determine a plurality of values for each parameter of said set,
  determining a level of drowsiness of the driver on the basis of the at least one value determined for each parameter of said set and of at least one predetermined threshold relating to said at least one parameter.

What is meant here by "in parallel" is, in a known manner, that the implementations are performed simultaneously.

The method according to an aspect of the invention advantageously makes it possible to determine the level of drowsiness of a vehicle driver (inversely proportional to their level of attention), according to parameters and values of parameters specific to said driver.

According to one aspect of the invention, the method comprises a step of warning the driver when the determined level of drowsiness is higher than a predetermined threshold. The method thus makes it possible to warn the driver in the event of drowsiness or low attention.

Preferably, the method comprises a warning step, after the detection of a high level of drowsiness of the driver.

Such a warning may consist of one or a combination of the following warning means: light signal, sound signal (for example the vehicle alarm), warning message displayed on a screen of the vehicle or sent to an external device, for example a smartphone, vibration of the seat or actuators (steering wheel or pedals).

Preferably, the predetermined duration of the learning phase of the method is between 5 and 20 minutes.

Such a duration makes it possible for the camera to generate a sequence of images with enough images to be analyzed in order to extract therefrom reliable information regarding the behavior of the driver, and to determine sets of parameters or values of parameters characteristic of said driver.

Preferably, the predetermined duration of the learning phase of the method is shorter than 20 minutes. Such a duration is sufficient to obtain the desired information regarding the driver, in other words to determine sets of parameters or of values of parameters that are characteristic of said driver, and to start the monitoring phase, in order to determine the level of drowsiness of the driver in real time.

Advantageously, the at least one parameter of each set used in the method is one from among the blink frequency of the driver's eyelids, the blink duration of the driver's eyelids, the blink amplitude of the driver's eyelids, the activity of the driver's face, the size of the contour of the driver's face, the height of the opening between the eyelids of each of the driver's eyes, the movements of the head with the amplitude and duration as main indicators. These parameters are simple parameters for detecting driver drowsiness levels.

Advantageously, the running of the predetermined algorithm performed in the monitoring phase is performed according to a plurality of implementations in parallel. Each implementation of the algorithm provides different indicators and analyses which relate to the majority of possible states of drivers. A single implementation of the algorithm cannot address all of the possibilities for detecting the level of drowsiness of the driver. The need to have a parallel implementation of the algorithm with different thresholds and parameters covers the majority of events and may provide the best warning in real time for the driver.

Advantageously, the monitoring phase may comprise a step of updating the degree of relevance for each implementation of the algorithm performed, the degrees of relevance remaining different from one another, the highest degree of relevance being assigned to the set of predetermined parameters and/or of predetermined ranges of values of parameters that is used for which the determined values of the parameters vary the least, in order to identify the reactions and attitude of the driver in question, in particular with regard to drowsiness and fatigue.

An aspect of the invention also relates to a computer of a vehicle, in particular a motor vehicle, making it possible to determine a level of drowsiness of a driver of said vehicle on the basis of a predetermined image analysis algorithm, the vehicle comprising a camera, said computer implementing said predetermined algorithm on the basis of a set comprising at least one parameter relating to the attitude of the driver, the computer being configured to:
in a learning phase performed for a predetermined period, preferably after each starting of the engine/motor of the vehicle:
receive a sequence of images of the driver generated by the camera, for example 10, 15, 20, 25, 30, 45, 60 . . . up to 200 images per second,
run the predetermined algorithm on said sequence of images generated in a plurality of implementations performed in parallel, each implementation using a different set of predetermined parameters and/or of predetermined ranges of values of parameters, so as to determine a plurality of values for each parameter of said set,
determine a different degree of relevance for each set used, the highest degree of relevance being assigned to the set of predetermined parameters and/or of predetermined ranges of values of parameters that is used for which the determined values of the parameters vary the least,
once the learning phase has ended, in a phase of monitoring the state of the driver:
receive a sequence of images of the driver generated by the camera,
run the predetermined algorithm on said sequence of images generated in at least one implementation on the basis of at least the set of parameters and/or of values of parameters having the highest degree of relevance, so as to determine a plurality of values for each parameter of said set,
determine a level of drowsiness of the driver on the basis of the at least one value determined for each parameter of said set and of at least one predetermined threshold relating to said at least one parameter.

The computer according to an aspect of the invention advantageously makes it possible to determine the level of drowsiness of a vehicle driver according to parameters and values of parameters specific to said driver. The computer thus makes it possible to warn the driver in the event of a high level of drowsiness of said driver.

Preferably, the predetermined duration of the learning phase is between 5 and 20 minutes.

Such a duration is sufficient to obtain the desired information regarding the driver, in other words to determine sets of parameters or of values of parameters that are characteristic of said driver, and to start the monitoring phase, in order to determine the level of drowsiness of the driver in real time. These parameters are simple parameters for detecting driver drowsiness levels.

Advantageously, the at least one parameter of each set used by the computer is one from among the blink frequency of the driver's eyelids, the blink duration of the driver's eyelids, the blink amplitude of the driver's eyelids, the activity of the driver's face, the size of the contour of the driver's face, the height of the opening between the eyelids of each of the driver's eyes, the movements of the head with the amplitude and duration as main indicators.

Preferably, the running of the predetermined algorithm performed by the computer in the step of carrying out the monitoring phase is performed according to a plurality of implementations in parallel. Each implementation provides different indicators and analyses which relate to the majority of possible states of drivers. A single implementation cannot address all of the possibilities for detecting the level of drowsiness or attention of the driver. The need to have a parallel implementation of the algorithm with different thresholds and parameters covers the majority of events and may provide the best warning in real time for the driver.

An aspect of the invention also relates to a vehicle, in particular a motor vehicle, comprising a camera configured to generate a sequence of images and a computer, such as described above, connected to said camera in order to receive said sequence of images.

BRIEF DESCRIPTION OF THE DRAWINGS

Other features and advantages of aspects of the invention will become apparent from the following description, given with reference to the appended figures, which are given by way of non-limiting examples and in which identical references are given to similar objects.

DETAILED DESCRIPTION OF THE PREFERRED EMBODIMENTS

The computer according to an aspect of the invention is intended to be mounted in a vehicle, in particular a motor vehicle, which may be manually driven or self-driving, in order to determine a level of drowsiness of the driver of said vehicle and to warn them or activate automatic driving if necessary. The level of drowsiness may correspond to a state (asleep, unconcentrated, alert, etc.) or a level which is quantized, for example alphanumerically, in order to define levels representing grades of drowsiness (for example, level 1 for an alert driver, level 2 for an unconcentrated driver, level 3 for a driver falling asleep, level 4 for a sleeping driver, etc.).

Figure 1:
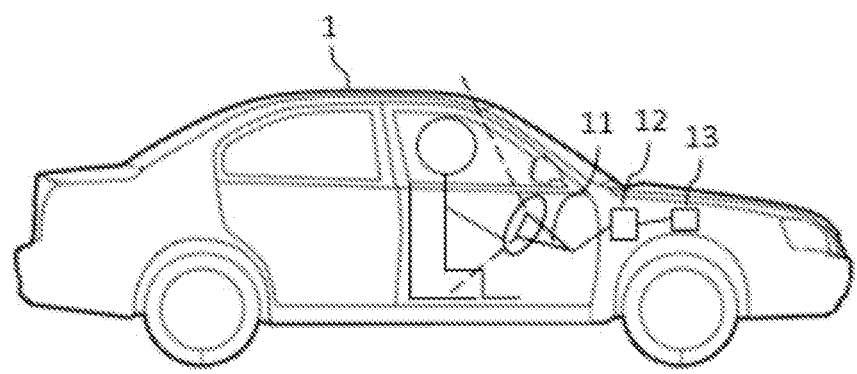
FIG. 1 schematically illustrates one embodiment of the vehicle according to an aspect of the invention.

With reference to FIG. 1, the device comprises a camera 11 installed in the vehicle 1, which films the driver, and a computer 12, also on board the vehicle 1, which processes the images generated by the camera 11.

The camera 11 is, for example, placed behind the driver's steering wheel and makes it possible to generate a sequence of images periodically, for example 10, 15, 20, 25, 30, 45, 60 . . . up to 200 images per second, showing the driver, preferably their face. The sequence of images is sent in real time to the computer 12 in order for said computer 12 to analyze said images.

The computer 12 is configured to implement a predetermined algorithm, on said sequence of images generated, in particular on one or more characteristic points (for example, the corner of the eyes, the position of the pupil, etc.) of the images of the sequence of images received, which it has determined in the images, in order to determine the level of drowsiness of the driver, i.e. to determine whether the driver is drowsy while driving the vehicle 1 and/or whether they are in a drowsy or distracted state.

The predetermined algorithm is implemented on the basis of a set comprising at least one parameter relating to the attitude of the driver at the wheel. These one or more parameters may be for example the blink frequency of the driver's eyelids, the blink duration of the driver's eyelids, the height of the opening of the driver's eyelids, the position of certain elements of the face (such as for example the ears, mouth, nose, etc.), the shape or size of the contour of the driver's face (in the case where the size of the contour of the face is small, it means that the driver is facing forward, and where it is large, that the driver is in profile), the activity of the driver's face, the movements of the head with the amplitude and duration as main indicators etc. In addition, the value of each parameter is also modifiable.

Each implementation of the algorithm is run in real time with a different configuration of the values for the decision-making thresholds. In order to have a robust function which will warn of driver drowsiness and thus make the method adaptive to each driver, it is necessary to look at the quality outputs for each different configuration. Depending on the learning phases, each threshold will be modified and personalized for the driver in question according to their behavior. The opening of the eyes, their blink duration, the eye closing and opening speed, the amplitude and speed of head movements are some of the parameters that may be used and adjusted in the learning phase.

The duration of the analysis time window is preferably set at the beginning for each implementation of the algorithm and various configurations are tested in the learning phase. The decision-making model is preferably based on the confidence indicators for each of the implementations and leads to a more robust warning than the conventional algorithms which lean on a single analysis.

The computer 12 is configured to, in a learning phase performed for a predetermined period, preferably after each starting of the engine/motor of the vehicle 1, receive a sequence of images of the driver generated by the camera 11, run the predetermined algorithm on said sequence of images generated in a plurality of implementations performed in parallel, each implementation using a different set of predetermined parameters and/or of predetermined ranges of values of parameters, so as to determine a plurality of values for each parameter of said set, and determine a different degree of relevance for each set used, the highest degree of relevance being assigned to the set of predetermined parameters and/or of predetermined ranges of values of parameters that is used for which the determined values of the parameters vary the least.

The computer 12 is configured to, once the learning phase has ended, in a phase of monitoring the state of the driver, receive a sequence of images of the driver generated by the camera 11, run the predetermined algorithm on said sequence of images generated in at least one implementation on the basis of at least the set of parameters and/or of values of parameters having the highest degree of relevance, so as to determine a plurality of values for each parameter of said set, and determine a level of drowsiness of the driver on the basis of the at least one value determined for each parameter of said set and of at least one predetermined attention threshold relating to said at least one parameter.

Preferably, the vehicle 1 further comprises an interface 13, for example on the dashboard of the vehicle 1, that allows in particular a warning message to be displayed or broadcast for the attention of the driver when their level of drowsiness is higher than a predetermined warning threshold.

Figure 2:
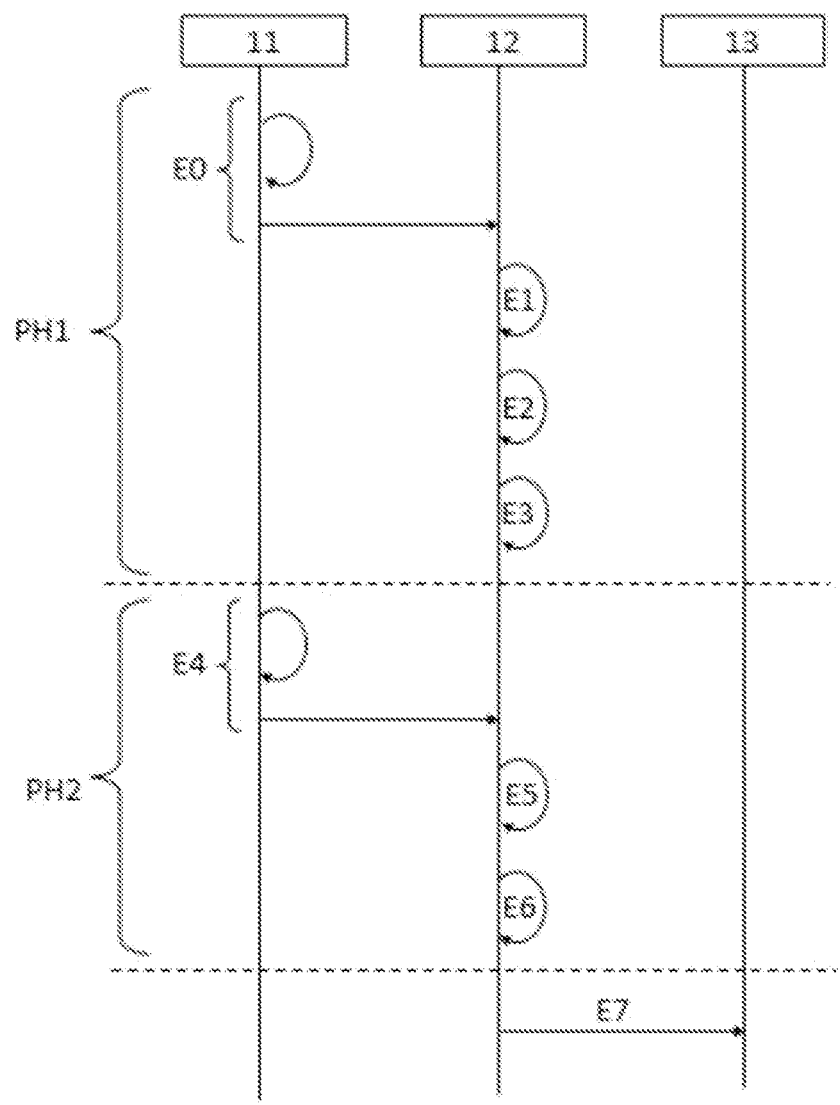
FIG. 2 shows one embodiment of the method according to an aspect of the invention.

An aspect of the invention will now be described in its implementation with reference to FIG. 2.

First of all, the method comprises what is called a "learning" phase PH1. This learning phase PH1 is preferably performed each time the engine/motor of the vehicle 1 is started.

The learning phase PH1 comprises a step E0 of generating a sequence of images using the camera 11. Said sequence of images generated, showing the driver, is then sent to the computer 12.

Next, in a determining step E1, the computer 12 determines one or more characteristic points of the images of the sequence of images generated, for example the corner of the eye, the position of the pupil, etc.

Next, the learning phase PH1 comprises a step E2 of the computer 12 running the predetermined algorithm on said sequence of images generated by the camera 11. The algorithm is executed a plurality of times in parallel and each implementation of said algorithm uses a different set of predetermined parameters and/or of predetermined ranges of values of parameters, so as to determine at least one value for each parameter of said set. Thus, each implementation is unique since it is performed on the basis of a different predetermined set of parameters and/or of values of parameters.

Lastly, the learning phase PH1 comprises a step E3 of determining a degree of relevance for each set used. In other words, this step makes it possible to class the one or more sets, on the basis of the implementations performed in the preceding step, from the most relevant to the least relevant with respect to the attitude of the driver, i.e. to prioritize the one or more sets that best describe the level of drowsiness or attention of the driver at the wheel of the vehicle 1 at that time.

Additionally, this determining step E3 also optionally comprises selecting the one or more sets, from among the plurality of sets, that is/are the most relevant. This selecting makes it possible either to know the one or more relevant sets to be considered by the method, or not to use the one or more least relevant sets, in other words the one or more sets which, after their respective implementation by the algorithm, represent the level of drowsiness of the driver inaccurately or overly approximately.

Thus, in this learning phase PH1, which preferably lasts between 10 and 15 minutes, the determining method makes it possible to determine the one or more sets, via their respective parameters or values of parameters, that is/are most capable of describing the behavior of a particular driver. Specifically, each driver has one or more specific sets allowing their behavior at the wheel to be to described. These one or more sets will therefore be used later on to determine the level of drowsiness of the driver.

Next, the method comprises what is called a "monitoring" phase PH2, subsequent to the learning phase PH1, which makes it possible to use the predefined algorithm combined with the one or more most relevant sets and/or the one or more sets selected previously. The monitoring phase PH2 may last for as long as the engine/motor of vehicle 1 is running. Said monitoring phase PH2 comprises a step E4 of generating a sequence of images of the driver using the camera 11. Said sequence of images generated, showing the driver, is then sent to the computer 12.

Next, the monitoring phase PH2 comprises a step E5 of continuously running the predetermined algorithm on the basis of said sequence of images generated in the monitoring phase PH2 and of the one or more most relevant sets or of the one or more sets selected in the learning phase PH1. Thus, in this running step E5, the computer 12 runs the predefined algorithm, thus making it possible to categorize the behavior of the driver according to various levels of drowsiness, from an alert level to an unalert level and lastly a drowsy level.

Having more than one set of parameters and/or of values of parameters adapted to the behavior of a driver at the wheel makes it possible, in the event of uncertainty, to use a plurality of sets to characterize the attitude of said driver, and thus to accurately determine their level of drowsiness. For example, if it is very sunny when the driver is driving the vehicle 1, this will force said driver to squint, so the eye opening is smaller than when there is no sun, but this does not indicate a state of drowsiness. Additionally, an illness might make the driver blink more often than usual, or, when the driver is at a red light, they might want to close their eyes for a few seconds to rest their eyes or stretch, this not indicating a level of drowsiness or a low level of attention either. There is therefore a need to use the predefined algorithm with a plurality of sets, comprising different parameters used, in order to confirm or disconfirm the level of drowsiness of the driver.

In step E5 of running the predetermined algorithm, said predetermined algorithm also makes it possible to update the one or more sets characteristic of each driver. Specifically, for example, in the case where the driver falls asleep at the wheel for a few seconds and then wakes up following external stimuli (such as for example the sound of the horn of another road user) the parameters or the values of parameters that are characteristic of the one or more relevant sets, and therefore adapted to the behavior of the driver, will be different before and after they fall asleep. Running step E5 therefore makes it possible to update the most relevant sets, in particular by modifying the order of relevance of the sets and also by updating parameters.

In said step E5 of running the predetermined algorithm, said predetermined algorithm, on the basis of the sets selected and updated, determines whether the driver is at a high level of drowsiness (i.e. low attention).

Next, the monitoring phase PH2 comprises a step E6 of determining a level of drowsiness of the driver, making it possible to categorize said level of drowsiness of the driver. By virtue of the plurality of sets adapted to each driver and the fact that the one or more sets are updated while the vehicle 1 is being used, it is simpler to obtain a diagnosis specific to the driver with a better level of accuracy.

Lastly, when a high level of drowsiness is detected, a warning signal is generated for the attention of the driver 1 in a warning step E7, which is outside the monitoring phase PH2. Preferably, the computer 12 sends a warning message to the interface 13, in order to warn the driver. This warning may take the form of a sound signal or of a light signal, for example an icon which lights up on the interface 13, a vibration of the seat or of the actuators (steering wheel, pedals). This step allows the driver's attitude to be categorized according to whether the driver is paying attention to driving, is inattentive/distracted or is drowsy. Each category may contain a plurality of levels.

As a variant, in the case where the vehicle 1 may be driven automatically in a self-driving mode, the computer 12 could order the switch to the self-driving mode when the driver is distracted or sinking into a state of drowsiness. In the case of switching to manual mode when the system cannot continue in self-driving mode, the state of the driver plays an important role and the system may decide to perform an emergency stop maneuver if the driver is not in a fit state to take back control.

One exemplary implementation of the method is described in the following paragraph. First of all, this example comprises a predetermined algorithm run, in the learning phase PH1, five times by the computer 12, on the basis of a sequence of images generated by the camera 11 and of five different predetermined sets of parameters and/or of values of parameters. The first set includes a parameter relating to the eye blink frequency with a threshold of 200 ms, above which the risk that the driver is in a drowsy state is high. The second set includes a parameter relating to the eye blink frequency with a threshold of 300 ms. The third set relates to the eye blink frequency, the threshold of which is 350 ms. The fourth set relates to a parameter regarding the eye blink frequency, the threshold of which is 400 ms, and a parameter relating to eye opening, the value of which is varied by the computer 11 in order to determine the most suitable one and the one that which will correspond best to the driver of the vehicle 1. Lastly, the fifth set relates to a parameter regarding head size, since the size of the head is smaller when facing forward than when the person is in profile. Thus, on the basis of said first, second, third, fourth and fifth sets, the detection method makes it possible to obtain the first, second, third, fourth and fifth implementations, respectively, each first, second, third, fourth and fifth set and each first, second, third, fourth and fifth implementation being unique and different from the others.

Next, the five sets obtained are prioritized according to their degree of relevance in step E3 of determining of the degree of relevance of learning phase PH1. It is considered that the order of relevance determined in this step, from the most relevant to the least relevant, is as follows: second set, fifth set, third set, fourth set, first set.

In addition, in this step, certain sets may be selected in order to use only the most relevant sets in the method, the sets that are not selected being deactivated. In the present case, it is considered that the second, fifth and third sets are selected.

Following this, the monitoring phase PH2 begins, in which a sequence of images is generated by the camera 11, then, on the basis of the sequence of images and of the second, fifth and third sets selected previously, the computer 12 determines the level of drowsiness of the driver. As mentioned above, it makes it possible to determine whether the driver is paying attention to driving, is inattentive/distracted or is drowsy.

In the event that the driver is not paying attention to their driving and/or they are in a confirmed state of drowsiness, a warning message is sent by the computer 12 to the interface 13, which warns the driver of their level of drowsiness for example by means of a light icon, a sound warning or a warning message. This warning stimulates the driver in the case that they are asleep, and/or advises them to stop. As a variant, a self-driving mode of the vehicle 1 could be activated.

An aspect of the invention therefore makes it possible to precisely determine a level of drowsiness of the driver so as to warn them or to hand the baton over to automatic driving.

The invention claimed is:

1. A method for determining a level of drowsiness of a driver of a motor vehicle, on the basis of a predetermined image analysis algorithm, said vehicle comprising a camera and a computer, said computer implementing said predetermined algorithm based on a set comprising at least one parameter relating to an attitude of the driver, the method, implemented by the computer, comprising:
   a) a learning phase performed for a predetermined duration, comprising the steps of:
      i) the camera generating a sequence of consecutive images of the driver,
      ii) determining at least one characteristic point of the images of the generated sequence of images,
      iii) during the learning phase, running the predetermined algorithm on the at least one characteristic point of the images of the generated sequence of images in a plurality of implementations performed simultaneously by the computer in order to perform a plurality of diagnostics, each implementation using a different set of at least one predetermined parameter and a different predetermined range of values for the at least one predetermined parameter, so as to determine a plurality of values for each parameter of said set,
      iv) determining a different degree of relevance for each implementation performed, the degrees of relevance being different from one another, a highest degree of relevance being assigned to the set of the at least one predetermined parameter and the different predetermined range of values for the at least one predetermined parameter for which the determined plurality of values for each parameter of said set vary the least,
   b) once the learning phase has ended, a phase of monitoring the state of the driver, comprising the steps of:
      i) the camera generating a sequence of images of the driver,
      ii) running the predetermined algorithm on said sequence of images generated in at least one implementation performed by the computer based on at least the set of the at least one predetermined parameter and the different predetermined range of values for the at least one predetermined parameter having the highest degree of relevance, so as to determine a plurality of values for each parameter of said set,
      iii) determining a level of drowsiness of the driver based on the plurality of values determined for each parameter of said set and of at least one predetermined threshold relating to said at least one parameter.

2. The method as claimed in claim 1, wherein the predetermined duration of the learning phase is between 5 and 20 minutes.

3. The method as claimed in claim 1, wherein the predetermined duration of the learning phase is shorter than 20 minutes.

4. The method as claimed in claim 1, wherein the at least one parameter of each set is one from among a blink frequency of the driver's eyelids, a blink duration of the driver's eyelids, a blink amplitude of the driver's eyelids, an activity of the driver's face, a size of a contour of the driver's face, a height of an opening between the driver's eyelids of each of the driver's eyes, movements of the driver's head with the blink amplitude and the blink duration as main indicators.

5. The method as claimed in claim 1, wherein the running of the predetermined algorithm is performed in the phase of monitoring the state of the driver in a plurality of implementations in parallel.

6. A computer of a vehicle, making it possible to determine a level of drowsiness of a driver of said vehicle based on a predetermined image analysis algorithm, the vehicle comprising a camera, said computer implementing said predetermined image analysis algorithm based on a set comprising at least one parameter relating to an attitude of the driver, the computer being configured to:
   a) in a learning phase performed for a predetermined period, preferably after each starting of the engine/motor of the vehicle:
      i) receive a sequence of images of the driver generated by the camera,
      ii) during the learning phase, run the predetermined algorithm on said generated sequence of images in a plurality of implementations performed simultaneously, each implementation using a different set of at least one predetermined parameter and a different predetermined range of values for the at least one predetermined parameter, so as to determine a plurality of values for each parameter of said set,
      iv) determine a different degree of relevance for each implementation performed, a highest degree of relevance being assigned to the set of the at least one predetermined parameter and the different predetermined range of values for the at least one predetermined parameter for which the determined plurality of values for each parameter of said set vary the least, b) once the learning phase has ended, in a phase of monitoring the state of the driver:
  i) receive a sequence of images of the driver generated by the camera,
  ii) run the predetermined algorithm on said sequence of images generated in at least one implementation on the basis of at least the set of the at least one predetermined parameter and the different predetermined range of values for the at least one predetermined parameter having the highest degree of relevance, so as to determine a plurality of values for each parameter of said set,
  iii) determine a level of drowsiness of the driver on the basis of the plurality of values determined for each parameter of said set and of at least one predetermined threshold relating to said at least one parameter.

7. The computer as claimed in claim 6, wherein the predetermined duration of the learning phase is between 5 and 20 minutes.

8. The computer as claimed in claim 6, wherein the at least one parameter of each set is one from among a blink frequency of the driver's eyelids, a blink duration of the driver's eyelids, a blink amplitude of the driver's eyelids, an activity of the driver's face, a size of a contour of the driver's face, a height of an opening between the driver's eyelids of each of driver's eyes, and movements of the driver's head with the blink amplitude and the blink duration as main indicators.

9. The computer as claimed in claim 6, wherein the predetermined algorithm is ran in the phase of monitoring the state of the driver in a plurality of implementations in parallel.

10. A vehicle comprising the camera and the computer as claimed in claim 6, the computer being connected to said camera.

11. The computer as claimed in claim 7, wherein the at least one parameter of each set is one from among a blink frequency of driver's eyelids, a blink duration of the driver's eyelids, a blink amplitude of the driver's eyelids, an activity of the driver's face, a size of a contour of the driver's face, a height of an opening between the driver's eyelids of each of the driver's eyes, and movements of the driver's head with the blink amplitude and the blink duration as main indicators.

12. The method as claimed in claim 1, wherein the at least one characteristic point of the images is one of a corner of the driver's eyes or a position of a pupil.

13. The method as claimed in claim 1, wherein each implementation uses a different set of a plurality of predetermined parameters.

14. The method as claimed in claim 1, wherein each implementation uses a different predetermined range of values for each of the predetermined parameters.

15. The method as claimed in claim 1, wherein a first set of the of at least one predetermined parameter includes a parameter relating to an eye blink frequency and at least one of a first predetermined threshold for the eye blink frequency or a second predetermined threshold for the eye blink frequency, and a second set of the of at least one predetermined parameter includes a parameter relating to the driver's head size and a third predetermined threshold for the driver's head size.

16. The method as claimed in claim 15, wherein the learning phase further comprises modifying and personalizing of the at least one of the first predetermined threshold for the eye blink frequency, the second predetermined threshold for the eye blink frequency, or the third predetermined threshold for the driver's head size based on a behavior of the driver.

17. The computer as claimed in claim 6, wherein a first set of the of at least one predetermined parameter includes a parameter relating to an eye blink frequency and at least one of a first predetermined threshold for the eye blink frequency or a second predetermined threshold for the eye blink frequency, and a second set of the of at least one predetermined parameter includes a parameter relating to the driver's head size and a third predetermined threshold for the driver's head size.

18. The computer as claimed in claim 17, wherein the learning phase further comprises modifying and personalizing of the at least one of the first predetermined threshold for the eye blink frequency, the second predetermined threshold for the eye blink frequency, or the third predetermined threshold for the driver's head size based on a behavior of the driver.

* * * * *